United States Patent [19]

Chang et al.

[11] Patent Number: 5,556,663
[45] Date of Patent: Sep. 17, 1996

[54] EXCIMER FLUORESCENCE METHOD FOR DETERMINING CURE OF COATINGS

[75] Inventors: Eng-Pi Chang, Arcadia; Yao-Feng Wang, Diamond Bar, both of Calif.; Mitchell A. Winnik, Ontario, Canada; Maris Ziemelis, Midland, Mich.

[73] Assignee: Avery Dennison Corporation, Pasadena, Calif.

[21] Appl. No.: 367,054

[22] Filed: Dec. 30, 1994

[51] Int. Cl.$^6$ .................................................. B05D 5/12
[52] U.S. Cl. ................................................ 427/8; 427/387
[58] Field of Search .......................... 427/8, 9, 10, 489, 427/503, 515, 387

[56] References Cited

U.S. PATENT DOCUMENTS

| | | | |
|---|---|---|---|
| 4,250,382 | 2/1981 | Libby | 250/302 |
| 4,651,011 | 3/1987 | Ors et al. | 250/459.1 |
| 4,656,049 | 4/1987 | Noto | 427/10 |
| 4,746,751 | 5/1988 | Oviatt, Jr. et al. | 556/456 |
| 4,866,152 | 9/1989 | Lo | 528/25 |
| 5,047,444 | 9/1991 | Devoe et al. | 522/99 |
| 5,107,008 | 4/1992 | Revis et al. | 556/425 |

OTHER PUBLICATIONS

Photophysical and Photochemical Tools in Polymeric Conformation Dynamics Morphology, Edited by M. A. Winnik, D. Reidel Publishing Company 1985, pp. 6, 7 and 98.

Excited State Dynamics in the Structural Characterization of Solid Alkyltrimethoxysilane–Derived Sol–Gel Films and Glasses Containing Bound or Unbound Chromophores. Chem. Mater. 6, 135–1357, Mar. 1994. Chambers et al.

Cyclization dynamics of polymers: 7. Applications of the pyrene excimer technique to the internal dynamics of poly-(dimethylsiloxane) chains. Polymer, 24, 319–322 (1983). Svirskaya et al.

The influence of polymer concentration on the internal motion–intramolecular pyrene excimer formation—of a low molecular weight probe in solution. Winnik et al, Polymer, 24, 473–475 (1983).

*Primary Examiner*—Shrive Beck
*Assistant Examiner*—Erma Cameron
*Attorney, Agent, or Firm*—Christie, Parker & Hale, LLP

[57] ABSTRACT

A fluorophore is added to or chemically attached to a curable release coating and the release coating is applied to a substrate. By exposing the release coating to an ultraviolet light source and measuring the intensity ratio of the dimer to monomer fluorescence, the cure of the release coating can be monitored. This method can be used as an on-line cure monitor in order to determine and control the extent of cure of coated substrates particularly silicone release liners.

40 Claims, No Drawings

EXCIMER FLUORESCENCE METHOD FOR DETERMINING CURE OF COATINGS

FIELD OF THE INVENTION

This invention relates to the use of excimer fluorescence techniques to monitor the cure of monomer/polymers, particularly silicone release coatings. A fluorescent group able to fluoresce in both the monomer and excimer states is chemically bonded to a portion of the uncured reactants for a polymerization reaction. Cure is monitored by exposing the reactants to an excitation light source and measuring its fluorescence in both the monomer and excimer states.

BACKGROUND OF THE INVENTION

Composite polymer structures are produced in a broad range of commercial settings. Often, a composite is formed by a polymerization reaction in which reactants are mixed together and then cured, for example, by the addition of catalyst and/or heat to promote the polymerization reactions. Proper curing is extremely important as the structure and properties of polymers strongly depend on the extent of cure.

One area where the monitoring of the cure of polymerization reactions is particularly important is in the area of polymer coatings. Often a large roll of substrate in the form of a web must be thoroughly and evenly coated with a polymer. The web of substrate is generally withdrawn from the roll and coated with a mixture of the appropriate reactants and catalyst as necessary for promoting the particular polymerization reaction. Such techniques are well-known in the art. The coated web is cured such as by passing it through a curing oven. The cured web is then either trimmed into final products or rolled up again for later use or further processing.

Silicone release liners are a class of coated substrate commonly used to protect pressure-sensitive adhesives and prevent the adhesive from inadvertently bonding to surfaces prior to application. Release liners are manufactured by applying a release coating onto a substrate or backing film, normally of paper. Various silicone compositions have long been used for the release coating. Certain release coatings are applied by dispersing the silicone composition in a solvent in order to reduce the viscosity to a point where the composition can be easily coated over the substrate. The release liner is then cured by heating to drive off the solvent and cause the silicone composition to crosslink. A pressure sensitive adhesive can then be applied to the cured release liner. The adhesive forms a limited bond to the resulting cross-linked silicone layer of the release liner.

Other release coatings use silicone compositions, such as polydimethylsiloxanes which have a sufficiently low viscosity to allow their application to a substrate without use of solvents. These solventless or 100% solid release coatings are mixed with a reactive cross-linker and cured by a Group VIII precious-metal catalyst, such as platinum. Upon application of heat, the catalyst promotes cross-linking of the silicone polymers, curing the release coating so that acceptable release properties are achieved.

Both solvent-applied and 100% solids release coating are able to protect a pressure sensitive adhesive until use because the adhesive forms a limited bond to the cross-linked silicone layer of the release liner. The release properties of the release liner can be modified by varying the cross-link density of the cured release coating. This occurs prior to application of the release liner to the pressure sensitive adhesive.

Release coatings are commercially manufactured in large quantities by using coating machines where large rolls of backing film, such as paper, are fed to a coating head where the release coating is applied. The coating is cured by passing the coated film through an oven. Proper cure is achieved by controlling either oven temperature or residence time of the coated film through the oven. Improper coating or cure of the release liner can adversely impact the performance of the pressure-sensitive adhesive. If the release coating cure is not complete, weld of the adhesive to the release liner can occur and the silicone can transfer to the pressure sensitive adhesive and adversely affect adhesive properties. On the other hand, overcure of the release liner may not adversely affect the release liner's properties, but will result in unnecessary expense.

Chapter 24 of the *Handbook of Pressure Sensitive Adhesive Technology*, Second Edition (1989), Edited by D. Satus provides an excellent summary of silicone release coating technology, and is incorporated herein by reference.

Currently, several methods exist for measuring whether proper cure of release liners has been achieved. Most of these methods, however, require a sample of the release liner, and cannot be performed while the coating apparatus is on-line. As a result, entire runs of release liner may need to be scrapped because an insufficient cure was not detected in time to adjust the product in process.

U.S. Pat. No. 5,107,008 to Revis et al. relates to curable fluorescent organopolysiloxane release coating compositions. These compounds when incorporated into the release coating provide fluorescence when exposed to ultraviolet light, which is different, and detectable apart, from the fluorescence that is produced by the paper-whitening components used in the paper industry. The fluorescence emission spectra of dansyl functional siloxanes compositions of that invention show a single emission wavelength maximum of 465 nanometers. There is no indication that those compositions exhibit dimer or excimer formation making those compositions inoperable under the instant invention. While the exposure to ultraviolet light of the cured coating is suggested as having utility for measuring coating thickness by measuring coating fluorescence, there is no suggestion regarding determination of degree of cure of the compositions on a substrate.

One on-line method of monitoring cure was recently disclosed in U.S. Pat. No. 5,047,444 to Devoe et al. This patent discloses the use of a latent fluorophore that is added to the release coating as a cure monitor. When subjected to the cure conditions, this cure monitor forms an ultraviolet detectable fluorophore. The cure is monitored by applying an ultraviolet light source of a particular wavelength to the release liner. The ultraviolet radiation is absorbed by the fluorophore which in turn emits radiation which can be detected by photosensing apparatus. The intensity of the emission can be used to determine whether proper cure has been achieved.

Despite being an improvement over the prior methods of cure determination, this method has certain deficiencies. For example, this method requires that the cure monitor be selected so that it has a comparable reaction rate to the cure rate of the release coating. Furthermore, the fluorophores added to the release coating as cure monitors often have very different physical properties from those of the silicone compositions in the release coating. Silicone compositions are generally nonpolar molecules with low surface energy.

Fluorophores, on the other hand, can be polar molecules with high surface energy. The differences in properties can lead to phase separation between the additive and the silicone compositions, causing skips in the coating application resulting in a release that is too tight, or otherwise incorrect determinations of cure.

Another on-line method of monitoring cure of polymers in general is disclosed in U.S. Pat. No. 4,651,011 to Ors et al. In this method, non reactive fluorophores are added to the polymer system to be cured. The polymer is exposed to polarized radiation of a wavelength that will excite the fluorophores causing them to fluoresce. The fluorescent emission is measured at two predetermined angles relative to the exciting radiation. Typically, one measurement is taken from an angle parallel to the exciting radiation and the other is taken perpendicular to the exciting radiation. These measurements indicate the orientation distribution of the fluorescent molecules in the polymer matrix. As the polymer cures and cross-linking proceeds, the fluorophores tend to assume some preferred orientation direction. The equation:

$$r = \frac{I_0 - I_{90}}{I_0 + 2I_{90}}$$

where $I_0$ and $I_{90}$ are the fluorescent intensities of the parallel and perpendicular emissions respectively can be used to determine the orientation distribution, r. The orientation distribution is in turn used to determine the cure of the release coating.

This method also has deficiencies in that the physical properties of the added fluorophore may be incompatible with those of the polymer matrix. This can cause phase separation between the components, or migration of the additive into the backing film when the method is used on release coatings. The result is undesirable release performance due to skips in the coating or incorrect determination of cure.

This invention is directed to the determination of the degree of cure in silicone release liner and other polymer coated substrate.

SUMMARY OF THE INVENTION

The present invention is directed to overcome the problems found in prior art monitoring methods. According to the present invention, there is added to a curable coating composition a small amount of at least one reactant of the curable polymer coating composition, preferably a reactive silicone polymer which is fluorescence-tagged and able to fluoresce in both the monomer and polymer states at different wavelengths. The composition is applied to a backing film, usually paper, by standard means and cured such as by passing the film through an oven. Upon leaving the oven, the release coating is exposed to an ultraviolet light source and the intensity of the resulting monomer and dimer emissions from the release coating are measured. By comparing the intensities of the monomer and dimer emissions, the degree of cure of the release coating can be determined. This is especially effective for thin coatings, in particular silicone polymer coatings for release films.

This method can be used as an on-line means to determine the degree of cure in the commercial manufacture of release liners on other coated substrate so that the curing operation can be mechanically controlled for optimal cure. For example, sensors can be used to determine the emission intensities sending signals to a controller that will compare the signals and adjust oven temperature or residence time of the oven to achieve proper cure.

By bonding the excimer to certain polymers used to form the cross-linked release or other coating, the cure monitor's physical properties can be made compatible with the release coating eliminating problems associated with incompatible additives. Furthermore, since the fluorescent emissions of the excimer are the result of the changing properties of the curing release or other coating rather than the result of a chemical reaction of the fluorophore itself, more accurate determinations of cure can be made and the fluorophore can be used for a broader range of different coating formulations than prior art cure monitoring methods. For example, the excimer can be chemically bonded to either solvent-based or solventless coatings with similarly attractive results.

A further advantage of this invention is that it is fully compatible with other on-line ultraviolet control methods. For example, fluorescent techniques are now used to determine thickness of release coatings. Fluorophores added to the release coating will emit radiation of an intensity that is proportional to the coating thickness. Sensors can be used to produce an electronic signal proportional to the emission intensity. A controller then uses this signal to make mechanical adjustments to the coating machine in order to maintain constant coating thickness. The excimers added to the release coating by this invention can be used to simultaneously determine coat weight, degree of cure, and skip.

It should be also clear that while the invention is described as relating to silicone release liners, the invention can be applied to various other coating operations where a silicone composition is applied to a substrate. For example, the invention can be used to monitor the cure of adhesives and coatings that do and do not contain silicone.

DESCRIPTION OF THE INVENTION

Certain fluorophores or excimers are able to fluoresce in both the monomer and dimer states when exposed to ultraviolet radiation. Each of these states emits radiation of a distinct wavelength or range of wavelengths. These fluorophores can be chemically attached to either the reactive siloxane polymers of a release coating, or the silicone hydride cross-linker of a release coating. They are preferably attached to the more compatible siloxane polymers to form a fluorescent tag sensor. Once these fluorophores have been chemically attached, normally about one to three fluorescent groups per polymer unit, they can be used to indirectly determine the degree of cure of the release coating by determining its viscosity. These compounds are able to determine viscosity because the dimerization of the fluorophore is diffusion-controlled. It should be noted that as used herein, the terms "dimer" and "dimerization" refer to the joining of two functional fluorescent groups or fluorophores to one another to cause a fluorescent emission that is different from that of a lone fluorophore which is referred to as a "monomer." Thus, the terms "monomer" and "dimer" refer to the orientation of the fluorphores with respect to one another, and do not refer to the number of fluorophores per polymer unit.

As the release liner is cured, its viscosity increases, limiting the diffusion of the fluorophore through the release coating. As a result, the ratio of the emission intensities of the monomer fluorescence and the dimer fluorescence increase rapidly during cure until a plateau is reached indicating completion of the cure.

Because measurements can be taken without physically contacting the film with mechanical measuring devices, the changing fluorescent properties of the curing release liner can be used to measure and control the curing step in a commercial manufacturing process. For example, an ultraviolet light source can be directed on the release coating as the release liner emerges from the curing oven. Sensors can then measure the intensity of both the monomer and dimer fluorescence emitted from the release coating. Output signals from the sensors can be used by a controller to calculate the ratio of monomer to dimer fluorescence, and determine whether proper curing has been achieved. The controller can then vary either the residence time or the temperature of the oven to ensure proper cure. Because a ratio of monomer to dimer emission intensity is measured rather than the absolute intensity, the degree of cure can be accurately monitored despite variations in coating thickness.

The excimer can be established in the release coating as a fluorescent silicone additive. However, in order to minimize problems associated with the possible incompatibility between the excimer and the release coating, in the preferred embodiment, the fluorescent groups are chemically attached to a portion of either the silicone polymers or the silicone hydride cross-linkers that make up the release coating. By chemically attaching the fluorescent group to the silicone compositions, problems associated with poor dispersion, phase separation or migration into the paper are minimized.

Since the chemical addition of a fluorescent group to an otherwise nonpolar silicone composition tends to increase its polarity, it is preferred that five or fewer fluorescent groups be added per polymer. At greater than five fluorescent groups, the increased polarity of the resulting polymer causes compatibility problems when mixed into a release coating. These problems include poor dispersion, phase separation and migration. About one to three fluorescent groups per polymer are preferred and about one fluorescent group per polymer is most preferred.

The fluorescence-tagged polymers of the present invention are generally pyrene-modified organopolysiloxane polymers having a formula selected from the group consisting essentially of

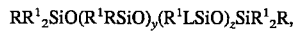

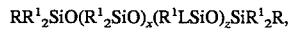

and

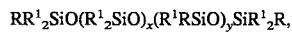

where: each $R^1$ is a radical independently selected from the group consisting essentially of alkyl radicals having 1 to 4 carbon atoms, and the phenyl radical; L is a fluorescent group, in this case, a silicon-bonded monovalent organic radical having the general formula $-R^2N=CHC_{16}H_9$ where $R^2$ is a divalent hydrocarbon radical and where $=CHC_{16}H_9$ is a pyrenylidene nucleus; each R is independently selected from the group consisting essentially of monovalent hydrocarbon radicals, monovalent halogenated hydrocarbon radicals, olefinic hydrocarbon radicals having 2 to 8 carbon atoms, the hydroxyl radical and the L radical; there being at least 2 reactive olefinic sites on average per molecule of said polymers and at least one L radical on average per molecule of said polymers and the sum of x+y+z has a value of at least one.

In the general formulae immediately above, when R denotes monovalent hydrocarbon or halogenated hydrocarbon radicals, the radicals are understood, for purposes of this invention, to be any silicon-bonded monovalent hydrocarbon or halogenated hydrocarbon radical which contains no aliphatic unsaturation and which has, preferably, no more than 20 carbon atoms, and most preferably from 1 to 6 carbon atoms.

Examples of monovalent hydrocarbon radicals which are encompassed by R include alkyl radicals, such as methyl, ethyl, and the straight- and branched-chain forms of propyl, hexyl, octyl, decyl and octadecyl; cycloaliphatic radicals, such as cyclohexyl; and radicals bearing an aromatic nucleus, such as phenyl, tolyl, benzyl, phenylethyl and xylyl.

Examples of halogenated hydrocarbon radicals which are encompassed by R include any of the hydrocarbon radicals encompassed above wherein one or more hydrogen atoms have been replaced with a halogen atom, preferably chlorine or fluorine. It is preferred that aliphatic carbon atoms of the halogenated hydrocarbon radicals which are directly bonded to or one carbon atom removed from a silicon atom not contain a halogen atom.

The aliphatic R radicals are preferably selected from the group of commercially used radicals such as methyl, phenyl, and perfluoroalkylethyl having the formula $CF_3(CF_2)_nCH_2CH_2-$ wherein n is an integer, preferably between 0 and 10, and most preferably between 0 and 4.

When the organopolysiloxane polymer is to be incorporated into an organic pressure sensitive adhesive-release coating composition the methyl radical constitutes at least 90 mol percent, and preferably at least 95 mol percent, of all hydrocarbon or halogenated hydrocarbon radicals of the polymers of this invention. When the organopolysiloxane polymer is to be incorporated into a silicone pressure sensitive adhesive-release coating composition, the perfluoroalkylethyl having the formula $CF_3(CF_2)_nCH_2CH_2-$, noted above, constitutes 5–50 mol percent, and preferably 10–25 mol percent, of all the hydrocarbon or halogenated hydrocarbon radicals.

Examples of olefinic hydrocarbon radicals encompassed by R include vinyl and the straight or branched-chain forms of allyl, butenyl, pentenyl, hexenyl and octenyl. It is preferred that at least two, and most preferably all, of the olefinic hydrocarbon radicals contain at least one vinyl radical. It is preferred that the olefinic radicals be selected from the group of commercially used reactive radicals such as vinyl and 5-hexenyl.

The organopolysiloxane polymers used in this invention must contain at least two, and preferably contain more than two, olefinic radicals in order to be useful as a reactive component in an addition-curing composition without substantially adversely affecting the cure of the composition.

Each $R^1$ in the above formula denotes a radical independently selected from the group consisting essentially of alkyl radicals having 1 to 4 carbon atoms or the phenyl radical. It is preferred that $R^1$ used in pressure sensitive release coating compositions be at least 90 mol percent and more preferably, at least 95 mol percent methyl radical.

Each L in the above formula denotes, independently, any silicon-bonded monovalent organic radical containing a fluorescent pyrene derivative having the general formula $R^2N=CHC_{16}H_9$ where $R^2$ is a divalent hydrocarbon radical and where $=CHC_{16}H_9$ is a pyrenylidene nucleus. For maximum hydrolytic stability it is preferred that L be bonded to Si by a silicon-carbon bond.

It is preferred that L contain a pyrene based radical, such as the pyrenylidene nucleus, since this radical provides preferred fluorescence for the organopolysiloxane compounds and compositions of this invention when exposed to ultraviolet light. The pyrene based radicals, when exposed to ultraviolet light, are able to fluoresce in both the monomer and dimer or excimer states. Each of these states emits radiation of a distinct wavelength or range of wavelengths.

For the purpose of this invention, a pyrenylidene nucleus has the formula $=CHC_{16}H_9$ and is bonded through its non-aromatic carbon atom to nitrogen.

In the preferred embodiments of this invention the monovalent organic radical bearing a pyrenylidene nucleus is bonded to a silicon atom by way of a divalent organic linking radical, one terminal of which is a carbon atom bonded to the silicone atom and the other terminal of which is a nitrogen atom bonded to the pyrenylidene nucleus. Examples of these divalent organic linking radicals include, but are not limited to, radicals having the formula $-R^2(NHR^2)_gNR^3-$ in which $R^2$ is a divalent hydrocarbon radical, $R^3$ is hydrogen or an alkyl radical having 1 to 6 carbon atoms and the subscript g has a value of 0 to 4. It is understood that polyamino linking radicals wherein g exceeds 0 may contain more than one pyrenylidene nucleus.

In preferred embodiments of this invention, the linking group is $-R^2NH$. In these embodiments $R^2$ is a divalent hydrocarbon group having from 3 to 6 carbon atoms such as trimethylene, tetramethylene or isobutylene. Examples are: $-CH_2CH_2CH_2NH-$, $-CH_2CH(CH_3)CH_2N(CH_3)-$, $-CH_2CH(CH_3)CH_2NH-$ and $-CH_2CH_2CH_2N(CH_3)-$.

The polysiloxanes of this invention preferably have the linear formula: $RR^1{}_2SiO(R^1{}_2SiO)_x(R^1RSiO)_y(R^1LSiO)_zSiR^1{}_2R$.

In this formula, each $R_1$ denotes a radical independently selected from the group consisting essentially of alkyl radicals having 1 to 4 carbon atoms, and the phenyl radical, each R denotes, independently, a radical selected from the group consisting essentially of monovalent hydrocarbon radicals, monovalent halogenated hydrocarbon radicals, olefinic hydrocarbon radicals, the hydroxyl radical and L radicals, noted above, including preferred embodiments.

For example, each terminal R radical can be a hydrocarbon radical, such as methyl, in which case the value of y must be at least two and the value of z must be at least one in order to provide the required number of L radicals and olefinic reaction sites. Alternatively, both terminal R radicals can be either L radicals or olefinic radicals thereby permitting, but not requiring, the value of y or z to be zero.

The average values of x, y and z can be zero or more provided that the organopolysiloxane contains at least one L radical and at least two olefinic reactive sites. The value of x typically ranges from 0–3000, preferably from 10–1000 and most preferably from 50–500. The values of y and z preferably range from 0–100 and most preferably from 0–10.

The sum of x+y+z must have a value of one or more. Its desired value will depend upon the use to which the organopolysiloxane is applied. However, for most applications, it is desired that the organopolysiloxane be a liquid, and preferably a flowable liquid, and an upper value for the sum of x+y+z of about 3000, preferably 500, and most preferably about 200 is appropriate. The organopolysiloxanes of this invention can have a viscosity ranging up to 100 million, most preferably from 10 to 10 thousand and for coating applications, from 100–1000 cP (centipoise) at 25° C.

Examples of preferred linear organopolysiloxanes of this invention include, but are not limited to, $(CH_3)_3SiO((CH_3)_2SiO)_x(CH_3ViSiO)_y(CH_3LSiO)_zSi(CH_3)_3$, $Vi(CH_3)_2SiO((CH_3)_2SiO)_x(CH_3ViSiO)_y(CH_3LSiO)_zSi(CH_3)_2Vi$, $Vi(CH_3)_2SiO((CH_3)_2SiO)_x(CH_3LSiO)_zSi(CH_3)_2Vi$, $L(CH_3)_2SiO((CH_3)_2SiO)_x(CH_3ViSiO)_y(CH_3LSiO)_zSi(CH_3)_2L$, and $L(CH_3)_2SiO((CH_3)_2SiO)_x(CH_3ViSiO)_ySi(CH_3)_2L$, wherein Vi is vinyl and x, y and z have values at least sufficient to provide the required number of fluorescent radicals and reactive olefinic sites.

Curable release coatings of the present invention generally comprise:

(A) 1 to 100 parts by weight of an organopolysiloxane compound having the general formula selected from the formula consisting essentially of one of:

$RR^1{}_2SiO(R^1{}_2SiO)_x(R^1RSiO)_y(R^1LSiO)_zSiR^1{}_2R$, $RR^1{}_2SiO(R^1RSiO)_y(R^1LSiO)_zSiR^1{}_2R$, $RR^1{}_2SiO(R^1{}_2SiO)_x(R^1LSiO)_zSiR^1{}_2R$, and $RR^1{}_2SiO(R^1{}_2SiO)_x(R^1RSiO)_ySiR^1{}_2R$, where: each $R^1$ is a radical independently selected from the group consisting essentially of alkyl radicals having 1 to 4 carbon atoms, and the phenyl radical, L is a silicon-bonded monovalent organic radical having the general formula $-R^2N=CHC_{16}H_9$ where $R^2$ is a divalent hydrocarbon radical and where $=CHC_{16}H_9$ is a pyrenylidene nucleus; each R is selected from the group consisting essentially of monovalent hydrocarbon radicals, monovalent halogenated hydrocarbon radicals, olefinic hydrocarbon radicals having 2 to 8 carbon atoms, the hydroxyl radical and the L radicals; there being at least 2 reactive olefinic sites on average per molecule of said polymers and at least one L radical on average per molecule of said polymers and the sum of x+y+z has a value of at least one;

(B) an amount of a methylhydrogen polysiloxane sufficient to provide from 0.8 to 4 silicon-bonded hydrogen atoms for every silicon-bonded olefinic radical in the composition;

(C) a hydrosilylation catalyst; and (D) 100 parts by weight of a dimethylmethylvinyl-polysiloxane.

In the curable compositions of this invention the fluorescent organopolysiloxane (A) can be any of the organopolysiloxanes of this invention, including preferred embodiments, herein delineated.

Component (B) of the curable compositions of this invention comprises one or more of the well-known coreactants that are used in addition-curing silicone compositions. By addition-curing it is meant a reaction which comprises hydrosilylation which leads to an increase in viscosity of the composition. Typically, the addition-curing composition is converted from the liquid or flowable state to the solid state or nonflowable state by this reaction. For adhesive-release coatings the addition-curing composition is sufficiently cured to provide no migration, no smear and no rub-off, as further defined below. Hydrosilylation is represented generically by the following scheme:

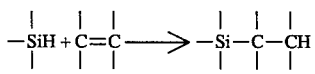

Component (B) can be any organopolysiloxane bearing at least two silicon-bonded hydrogen radicals which are reactive, in hydrosilylations, with the silicon-bonded reactive olefinic radicals of component (A). Component (B) preferably has a viscosity at 25° C. of from 1 to 1000 cP. In terms of preferred monovalent hydrocarbon radicals, noted above, examples of organohydrogenpoly-siloxanes which are suitable as component (B) for the compositions of this invention include:

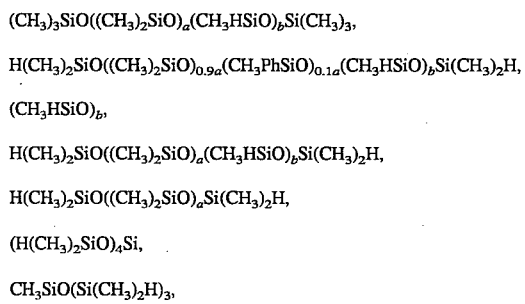

and (CH$_3$)$_3$Si(CH$_3$HSiO)$_b$Si(CH$_3$)$_3$, where Ph is phenyl, and the values of the subscripts a and b can be zero or greater, and the sum of a and b has a value up to about 3000.

Hydrosilylation catalyst component (C) can be any of the platinum group metal-containing materials which catalyze the reaction of silicon-bonded hydrogen atoms with silicon-bonded olefinic hydrocarbon radicals. Component (C) is preferably a platinum- or rhodium-containing material which is used in addition-curing silicone coating compositions. Examples thereof include, but are not limited to, chloroplatinic acid and its compounds and complexes, and rhodium trichloride and its compounds and complexes. U.S. Pat. No. 5,107,008 hereinabove incorporated discloses platinum group metal-containing catalysts that are suitable for use as component (C) in the curable compositions of this invention.

Component (C) is most preferably selected from platinum-containing catalysts since they are most widely used and available and because they provide a more favorable effect for the compositions of this invention in terms of pot life and cure time. A preferred platinum-containing catalyst component in the compositions of this invention is a form of chloroplatinic acid, either as the commonly available hexahydrate form or as the anhydrous form, because it is easily dispersible in organosilicon systems.

A particularly useful catalyst is the composition obtained when chloroplatinic acid is reacted with an aliphatically unsaturated organosilicon compound such as divinyltetramethyldisiloxane, as disclosed by U.S. Pat. No. 3,419,593 incorporated herein by reference.

The amount of platinum group metal-containing catalyst component (C) that is used in the compositions of this invention is not narrowly limited as long as there is a sufficient amount to accelerate a room temperature reaction between the silicon-bonded hydrogen atoms and the silicon-bonded olefinic hydrocarbon radicals of the reactive component. The exact necessary amount of said catalyst component will depend upon the particular catalyst. However, for chloroplatinic acid said amount can be as low as one part by weight of platinum for every one million parts by weight of organosilicon components. Preferably said amount is at least 10 parts by weight, on the same basis.

Organopolysiloxane component (D) can be any organopolysiloxane bearing at least two silicone-bonded olefinic radicals which are reactive in hydrosilylations, with the silicon-bonded reactive radicals of component (B). Component (B) has a viscosity at 25° C. of from 100 cP to 100 million cP and more. In terms of preferred monovalent hydrocarbon radicals, noted above, examples of linear organopolysiloxanes which are suitable as component (D) for the compositions of this invention include:

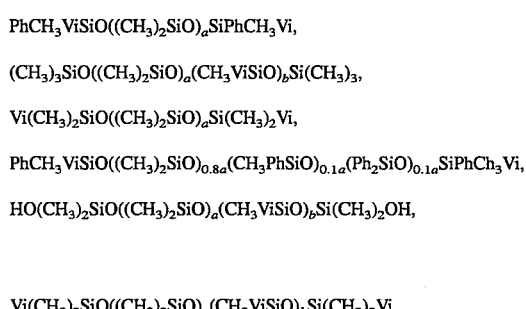

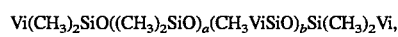

and

Vi(CH$_3$)$_2$SiO((CH$_3$)$_2$SiO)$_a$(CH$_3$ViSiO)$_b$Si(CH$_3$)$_2$Vi, where Vi and Ph denote vinyl and phenyl, respectively. The values of the subscripts a and b can be zero or greater; however, the sum of a plus b has a value of up to about 3000.

The amounts of organopolysiloxane components to be used in the compositions of this invention are substantially the same as the amounts used in addition-curable organopolysiloxane compositions of the art. Typically, the amounts of organohydrogenpolysiloxane and olefin-containing organopolysiloxane components to be used are expressed in terms of the mole ratio of silicon-bonded hydrogen atoms to silicon-bonded olefin radicals. This ratio has a value of from about 0.1/1 to 10/1, preferably 0.51/1 to 5/1 and most preferably 1/1 to 4/1.

In preferred embodiments of the invention, it is desirable to have an inhibitor component present, which can be any of the materials that inhibit the catalytic activity of the platinum group metal-containing catalysts at room temperature but not at elevated temperature. Inhibitors for the platinum group metal-containing catalysts are well known in the organosilicon art as discussed in U.S. Pat. No. 5,107,008 hereinabove incorporated. Examples of various classes of such metal catalyst inhibitors include unsaturated organic compounds such as ethylenically or aromatically unsaturated amides, acetylenic compounds, ethylenically unsaturated isocyanates, olefinic siloxanes, unsaturated hydrocarbon diesters, and conjugated ene-ynes among others.

The amount of inhibitor component to include in the curable compositions of this invention is not critical and can be any amount that will provide the desired inhibition, if any, of the hydrosilylation curing reaction at room temperature, but not so much as to prevent said curing reaction at useful elevated temperatures. To determine an optimum amount of inhibitor, one may simply add an arbitrary amount thereof, such as from 0.1 to 10 percent by weight, based on the weight of the curable components in the composition, observe the effect of such an amount on the curing behavior of the composition and adjust the amount of inhibitor in the next composition as desired. Generally, the degree of inhibition is directly related to the amount of inhibitor present in the composition.

The amount of fluorescent organopolysiloxane compounds to be used in the compositions is not critical, as long as there is a sufficient amount to permit its fluorescence to be detected in a useful manner, such as for detecting the presence of, measuring the amount of, and/or measuring the degree of cure of, the composition.

While the amount of organopolysiloxane components of the compositions of this invention can all contain fluorescent radicals, it is only necessary for a portion of the olefin radical-containing organopolysiloxane component to contain fluorescent radicals.

It is preferred that an amount of pyrenylidene containing organopolysiloxane, such as from 1–49 weight percent, be used in combination with from 51–99 weight percent of an organopolysiloxane which contains the same type of reactive sites, but is free of pyrenylidene radicals; both percentages being based on the total amount of organopolysiloxane which contains the reactive olefinic radicals. For example, an organopolysiloxane composition of this invention comprises from 1–49 parts by weight of an organopolysiloxane bearing pyrenylidene radicals and vinyl reactive sites and an amount of a pyrenylidene radical-free organopolysiloxane bearing vinyl reactive sites sufficient to provide 100 parts by weight of organopolysiloxanes bearing vinyl reactive sites. In order to further avoid compatibility problems between the pyrenylidene containing organopolysiloxanes and the organopolysiloxanes free of pyrenylidene radicals, and other problems that are discussed in more detail in the examples, it is preferred that the pyrenylidene containing organopolysiloxanes comprise less than about 20 parts by weight to the total organopolysiloxanes.

The curable compositions of this invention can further comprise optional components, such as diluents, solvents, fillers, cure control additives, adhesive-release additives, surfactants and wet-out additives, which are well known in the silicone coatings art, and particularly in the adhesive-release coatings art.

The curable compositions of this invention can be prepared by any suitable method, for example, as disclosed in U.S. Pat. No. 5,107,008 hereinabove incorporated. When preparing a curable composition of this invention it is preferred to bring together component (C) and the SiH-containing component (B) in a final mixing step just before the composition is to be used.

The curable compositions described are particularly useful in coating processes where a thin layer of curable composition is applied to a substrate and thereafter cured. Examples of curable silicone coatings in which the curable compositions are useful include silicone adhesives, waterproof silicone coatings, and, of course, silicone release liners. The fluorescent behavior of said compositions allow for the qualitative detection and, with proper calibration of the composition-substrate combination and the use of well-known fluorescence measuring methods, the quantitative detection and application control of the coating. Thus, a solution to a major problem in the silicone coatings art has been provided by the present invention.

In particular, the curable compositions are useful for measuring whether proper cure of thin film release liners has been achieved. Since the pyrene-based functional coatings are able to fluoresce in both the monomer and dimer states at different wavelengths when the coatings are exposed to an ultraviolet light source, the intensity of the resulting monomer and dimer emissions from the release coating can be measured. By comparing the intensities of the monomer and dimer emissions, the degree of cure of the release coating can be determined. This is especially effective for thin coatings.

The following examples are disclosed to illustrate the invention and are not to be regarded as limiting. All parts and percentages are by weight, unless otherwise specified, and temperatures are degrees Celsius, Vi denotes vinyl and Ph denotes phenyl. Viscosities were measured with a rotating spindle viscometer.

Cure time for a composition means the time interval required for the composition, when coated onto 37 lb. Nicolet supercalendered kraft paper using a laboratory trailing blade coater adjusted to 25 psi blade pressure to attain the no smear, no migration, no rub-off condition.

The no smear condition was determined by lightly streaking the coating with a finger and observing for the absence of haze in the streaked area.

The no migration condition was determined by firmly adhering a common, pressure sensitive adhesive tape to the coating, removing the tape and folding the removed tape together, adhesive surfaces to each other. Absence of migration of the coating to the tape was indicated by noting that the doubled tape was as difficult to separate as unused tape so doubled.

The no rub-off condition was determined by vigorously rubbing the coating with the index finger and noting that the coating could not be removed from the paper.

Visual inspection of the bulk compositions for appearance was made prior to coating as a thin film on paper. The range used for inspection was from transparent or clear to insoluble, with clear indicating that the pyrenylidene functional siloxane was compatible or highly dispersed in the coating composition and insoluble indicating the formation of small droplets or complete phase separation within a few minutes. Hazy, the mid-range value, indicated that the pyrenylidene functional siloxane was still dispersible in the coating composition and stable for at least several hours upon standing at ambient conditions in a closed container.

EXAMPLES 1–5

Four coating compositions were prepared by mixing predetermined amounts of the following pyrenylidene functional siloxanes:

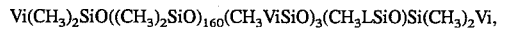

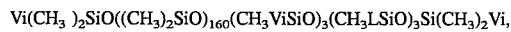

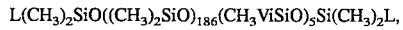

and

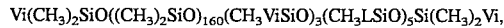

where L denotes the $-CH_2CH_2CH_2N=CHC_{16}H_9$ radical in which $=CHC_{16}H_9$ is a pyrenylidene nucleus, with an adhesive release coating composition, designated composition A, which cures to an adhesive release coating when mixed with an organohydrogen polysiloxane and heated, and which contained 97.1 parts of a vinyl-terminated dimethyl-methylvinyl siloxane copolymer containing 1.1 mol % vinyl radicals, 1.85 parts of a platinum-coating curing catalyst and 1.05 parts of a platinum catalyst inhibitor which is effective at room temperature but not at elevated temperature. Examples 1 to 4 correspond to the above compositions respectively.

In addition, for Example 5, a pyrenylidene containing siloxane trimer having no vinyl functionality was incorporated into composition A. This pyrenylidene had the average formula $(CH_3)_3SiO(CH_3LSiO)SiO(CH_3)_3$, where L denotes the —$CH_2CH_2CH_2N=CHC_{16}H_9$ radical in which =$CHC_{16}H_9$ is a pyrenylidene nucleus. This fluorescent siloxane was designated Siloxane (i).

These coating compositions were applied to 37 lb. Nicolet supercalendered kraft paper, using a laboratory trailing blade coater adjusted to 25 psi blade pressure. The coated papers were heated in a forced air oven at various temperatures to cure the coating to a condition of no smear, no migration and no rub-off described hereinabove. The cured coatings exhibited a green fluorescence when viewed under ultraviolet light. The compositions and their cure profiles were compared against a comparison composition of the same formulation without the addition of the fluorescent additive to serve as a control. The comparison composition was comprised of 100 parts of composition A and 3 parts of an organohydrogen polysiloxane cross-linker. Table 1 shows the cure profiles of these compositions and the appearance of the coatings as made by visual inspection prior to coating onto the paper, described hereinabove. The fluorescent coating compositions were yellow in color prior to coating. The comparison composition was colorless and clear in appearance. These Examples demonstrate the utility of the compositions of this invention as a fluorescing adhesive release coating which provides undiminished adhesive releasing ability and demonstrates the necessity of having the pyrenylidene functional siloxane reacted into the release coating to prevent transfer of the fluorescent siloxane to the adhesive tape brought into releasable contact with the cured coating.

TABLE I

| Component | Ex 1 | Ex 2 | Ex 3 | Ex 4 | Ex 5 |
|---|---|---|---|---|---|
| | | | Amount, parts | | |
| Composition A | 83.0 | 83.0 | 83.0 | 96.3 | 99.3 |
| Cross-linker | 3.0 | 3.0 | 3.0 | 3.0 | 3.0 |
| Example 1 | 17.0 | | | | |
| Example 2 | | 17.0 | | | |
| Example 3 | | | 17.0 | | |
| Example 4 | | | | 3.7 | |
| Siloxane (i) | | | | | 6.8 |
| Property | | | Observed Value | | |
| Appearance | Clear | Hazy | Clear | Hazy | |
| Cure Profile*, °C./sec | 110/60 | 120/60 | 120/60 | 110/60 | |

*Control = 100/30

Visual examination of the adhesive tape under an ultraviolet light was used to determine the no migration condition, and showed no indication of transfer of fluorescence to the adhesive backing for Examples 1 through 4. Example 5 showed fluorescence under an ultraviolet light indicating transfer to the adhesive backing. Example 5 is not within the scope of the present invention.

EXAMPLE 6

This example demonstrates the use of the fluorescent-tagged polymer as a cure sensor. The fluorescent organopolysiloxane from Example 1 was mixed with an adhesive release coating composition comprising 97.1 parts of a vinyl-terminated dimethylmethylvinyl siloxane copolymer containing 1.1 mol % vinyl radicals, 1.85 parts of a platinum-containing curing catalyst, 1.05 parts of a platinum catalyst inhibitor which is effective at room temperature but not at elevated temperature and 3 parts of a methylhydrogen polysiloxane. This resulted in a formulation having a clear appearance when evaluated visually as described hereinabove. This mixture was coated onto BG-50 paper and cured at 130° C. During cure, periodic measurements of the intensity of the monomer and dimer fluorescent emissions were taken using a fluorometer. This polymer, when exposed to a 330 nm ultraviolet light source showed a dimer emission at about 500 nm and a monomer triplet emission at about 382, 400, and 415 nm, with the most prominent peak at 400 nm. The ratio of monomer to dimer emission intensities started at 0.7 and rapidly increased to a plateau at about 2.5. At this point tests described hereinabove on the release liner showed that cure was complete as indicated by a condition of no smear, no migration and no rub-off.

At relatively thin coating thicknesses (on the order of 1 micron) such as are preferred in the commercial production of release liners, tests have shown that the emission signal for the dimer becomes rather indistinct. This is presumably due to interferences such as might be caused by fluorescent characteristics of the backing paper. However, methods are available to "clean up" the signal by using multiple or repetitive scans and a computer to filter noise, or by using peak deconvoluting software to resolve and enhance the dimer signal. For on-line measurement of degree of cure, the preferred embodiment employs such measures to improve the sensitivity and accuracy of the measurements.

Tests have also shown that release liners made with high concentrations of the excimer-modified silicone polymers may exhibit poor release properties compared to the unmodified polymers. The release value (using a Tag and Label Manufacturers Institute Tester at 300 in/min) for a 50% mixture of modified polymer in unmodified polymer was about four times as high as the release value for unmodified polymer when emulsion acrylic adhesives were adhered to the release liner. When a solvent rubber-based adhesive was adhered to a 50% mixture of modified polymer in unmodified polymer, release values double those for the unmodified polymer were measured. However, at concentrations of modified polymer less than about 20%, no significant changes in release values were measured. Therefore, in the preferred embodiment of the invention, loadings of the modified polymer are limited to less than 20% of the total release coating.

What is claimed is:

1. A method for determining the degree of cure of a polymer coating formed by the polymerization of a curable coating mixture of reactants comprising the steps of:

(a) adding to the coating mixture an amount of a fluorescent modified reactant that comprises one of the reactants of the coating mixture having added thereto by chemical reaction, a fluorescent tag that is able to fluoresce in both monomer and excimer states;

(b) applying the coating mixture containing the fluorescent modified reactant to a substrate to form a coated film;

(c) curing the coated film;

(d) exposing the coated film to an excitation light source;

(e) measuring the intensity of the emissions from the fluorescent modified reactant contained in the coated film in each of the monomer and excimer emission states; and (f) comparing the intensity of the monomer emission to the intensity of the excimer emission to determine degree of cure.

2. The method set forth in claim 1 further comprising the step of using the determination of the degree of cure for controlling cure of the coated film.

3. The method set forth in claim 1 wherein the fluorescent modified reactant is a polymer that contains an average of between about one and about five fluorescent tags per molecule.

4. The method set forth in claim 1 wherein the fluorescent modified reactant contains an average of between about one and about three fluorescent tags per molecule.

5. The method set forth in claim 1 wherein each fluorescent modified reactant contains an average of about one fluorescent tag per molecule.

6. The method set forth in claim 1 wherein the amount of fluorescent modified reactant added to the coating mixture is less than about 50% by weight of the coating mixture.

7. The method set forth in claim 6 wherein the amount of fluorescent modified reactant added to the coating mixture is less than about 20% by weight of the coating mixture.

8. The method set forth in claim 1 wherein the fluorescent tag comprises a radical containing a pyrenyl group.

9. A method for determining the degree of cure of a polymer that is to be formed by the polymerization of a mixture of reactants comprising the steps of:
  (a) adding to the mixture an amount of a fluorescent modified reactant that comprises one of the reactants in the mixture to which a pyrenyl radical is added by chemical addition, said fluorescent modified reactant being capable of fluorescing in both monomer and excimer states;
  (b) coating the mixture onto a substrate;
  (c) curing the mixture;
  (d) exposing the mixture to an excitation light source to cause the reactant to fluoresce in the monomer and excimer states;
  (e) measuring the intensity of the fluorescent emissions from the mixture in each of the monomer and excimer emission states; and
  (f) comparing the intensity of the monomer emission to the intensity of the excimer emission to determine degree of cure.

10. The method set forth in claim 9 further comprising the step of using the determination of the degree of cure for controlling cure of the mixture.

11. The method set forth in claim 9 wherein an average of between about one and about five pyrenyl radicals are chemically added to each molecule of the flourescent modified reactant.

12. The method set forth in claim 11 wherein an average of between about one and about three pyrenyl radicals are chemically added to each molecule of the flourescent modified reactant.

13. The method set forth in claim 12 wherein an average of about one pyrenyl radical is chemically added to each molecule of the flourescent modified reactant.

14. The method set forth in claim 9 wherein the amount of flourescent modified reactant added to the mixture is less than about 50% by weight of the mixture.

15. The method set forth in claim 9 wherein the amount of flouresent modified reactant added to the mixture is between about 15% and about 20% by weight of the mixture.

16. A method for determining the degree of cure of a silicone coating comprising:
  adding an amount of a reactive fluorescence-tagged silicone polymer able to fluoresce in both monomer and dimer states to a silicone coating mixture;
  applying the coating mixture to a substrate to form a coated film;
  curing the coated film;
  exposing the coating to an ultraviolet light source;
  measuring the intensity of the emissions from the coated film in both of the monomer and dimer emissions states; and
  comparing the intensity of the monomer emissions to the intensity of the dimer emissions.

17. The method set forth in claim 16 wherein the determination of the degree of cure is used for controlling the means for promoting cure.

18. The method set forth in claim 16 wherein the fluorescence-tagged silicone polymer comprises silicone polymers used in the coating mixture.

19. The method set forth in claim 16 wherein the fluorescence-tagged silicone polymer comprises a fluorescent tagged silicone hydride cross-linker used in the coating mixture.

20. The method set forth in claim 16 wherein each fluorescence-tagged silicone polymer contains between about one and about five fluorescent tags per molecule.

21. The method set forth in claim 20 wherein each fluorescence-tagged silicone polymer contains from between about one and about three fluorescent tags per molecule.

22. The method set forth in claim 21 wherein each fluorescence-tagged silicone polymer contains about one fluorescent tag per molecule.

23. The method set forth in claim 16 wherein the amount of fluorescence-tagged silicone polymer is less than about 50% by weight of the coating mixture.

24. The method set forth in claim 23 wherein the amount of fluorescence-tagged silicone polymer is less than about 20% by weight of the coating mixture.

25. The method set forth in claim 16 wherein the fluorescence-tagged silicone polymer consists of a pyrene-modified silicone polymer.

26. The method set forth in claim 16 wherein the silicone coating is a release coating for use with a pressure sensitive adhesive.

27. The method set forth in claim 16 wherein the fluorescence-tagged silicone polymer consists of a polymer selected from the group consisting essentially of:

$$RR^1_2SiO(R^1_2SiO)_x(R^1RSiO)_y(R^1LSiO)_zSiR^1_2R, \quad (i)$$

$$RR^1_2SiO(R^1RSiO)_y(R^1LSiO)_zSiR^1_2R, \quad (ii)$$

$$RR^1_2SiO(R^1_2SiO)_x(R^1LSiO)_zSiR^1_2R, \quad (iii)$$

and $$RR^1_2SiO(R^1_2SiO)_x(R^1RSiO)_ySiR^1_2R, \quad (iv)$$

wherein:
  each $R^1$ is a radical independently selected from the group consisting essentially of alkyl group containing from 1 to about 4 carbon atoms and phenyl radical;
  L is a silicon-bonded monovalent organic radical having the formula —$R^2N=CHC_{16}H_9$, wherein $R^2$ is a divalent hydrocarbon radical, and =$CHC_{16}H_9$ is a pyrenylidene nucleus; and
  each R is independently selected from the group consisting of monovalent hydrocarbon radicals, monovalent halogenated hydrocarbon radicals, olefinic hydrocarbon radicals having 2 to 8 carbon atoms, the hydroxyl radical, and the L radicals; wherein the sum of x+y+z has a value of at least one and said polymer has an average of at least two reactive olefinic sites.

28. A method for determining the degree of cure of a silicone coating comprising:
  adding an amount of fluorescence-tagged silicone polymer able to fluoresce in both monomer and dimer states to a silicone coating mixture wherein each fluorescence-tagged silicone polymer includes about one fluorescent group per molecule and the amount of fluorescence-tagged silicone polymer is less than about 20% by weight of the silicone release coating mixture;

applying the coating mixture to a backing film substrate to form a coated film;

curing the coated backing film;

exposing the coated backing film substrate to an ultraviolet light source;

measuring the intensity of the emissions from the coated backing film in both of the monomer and dimer emissions states; and comparing the intensity of the monomer emissions to the intensity of the dimer emissions to determine degree of cure.

29. The method set forth in claim 28 wherein the determination of the degree of cure is used for controlling the means for promoting cure.

30. The method set forth in claim 28 wherein the fluorescence-tagged silicone polymer consists of a pyrene-modified silicone polymer.

31. The method set forth in claim 28 wherein the silicone coating is a release coating for use with a pressure sensitive adhesive.

32. The method set forth in claim 28 wherein the fluorescence-tagged silicone polymer consists of a polymer selected from the group consisting essentially of:

$RR^1_2SiO(R^1_2SiO)_x(R^1RSiO)_y(R^1LSiO)_zSiR^1_2R,$ (i)

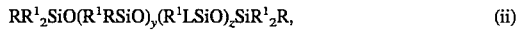

$RR^1_2SiO(R^1RSiO)_y(R^1LSiO)_zSiR^1_2R,$ (ii)

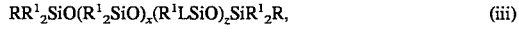

$RR^1_2SiO(R^1_2SiO)_x(R^1LSiO)_zSiR^1_2R,$ (iii)

and

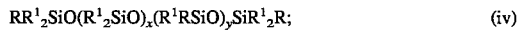

$RR^1_2SiO(R^1_2SiO)_x(R^1RSiO)_ySiR^1_2R;$ (iv)

wherein:

each $R^1$ is a radical independently selected from the group consisting essentially of alkyl radicals having 1 to 4 carbon atoms and the phenyl radical;

L is a silicon-bonded monovalent organic radical having the formula $—R^2N=CHC_{16}H_9$, wherein $R^2$ is a divalent hydrocarbon radical, and $=CHC_{16}H_9$ is a pyrenylidene nucleus; and each R is independently selected from the group consisting of monovalent hydrocarbon radicals, monovalent halogenated hydrocarbon radicals, olefinic hydrocarbon radicals having 2 to 8 carbon atoms, the hydroxyl radical and the L radicals; wherein the sum of x+y+z has a value of at least one and said polymer having an average of at least two reactive olefinic sites.

33. A method for determining the degree of cure of a silicone coating comprising:

adding an amount of a fluorescence-tagged silicone reactant able to fluoresce in both monomer and excimer states to a curable silicone coating composition mixture, said reactant selected from the group consisting essentially of:

$RR^1_2SiO(R^1_2SiO)_x(R^1RSiO)_y(R^1LSiO)_zSiR^1_2R,$ (i)

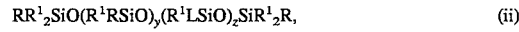

$RR^1_2SiO(R^1RSiO)_y(R^1LSiO)_zSiR^1_2R,$ (ii)

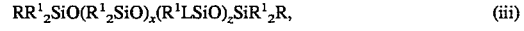

$RR^1_2SiO(R^1_2SiO)_x(R^1LSiO)_zSiR^1_2R,$ (iii)

and

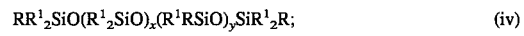

$RR^1_2SiO(R^1_2SiO)_x(R^1RSiO)_ySiR^1_2R;$ (iv)

wherein:

each $R^1$ is a radical independently selected from the group consisting essentially of alkyl radicals having 1 to 4 carbon atoms and the phenyl radical;

L is a silicon-bonded monovalent organic radical having the formula $—R^2N=CHC_{16}H_9$, wherein $R^2$ is a divalent hydrocarbon radical, and $=CHC_{16}H_9$ is a pyrenylidene nucleus; and each R is independently selected from the group consisting of monovalent hydrocarbon radicals, monovalent halogenated hydrocarbon radicals, olefinic hydrocarbon radicals having 2 to 8 carbon atoms, the hydroxyl radical and the L radicals; wherein the sum of x+y+z has a value of at least one and said reactant having an average of at least two reactive olefinic sites;

(b) coating the mixture onto a substrate;

(c) curing the mixture;

(d) exposing the mixture to an excitation light source to cause the reactant to fluoresce in the monomer and excimer states;

(e) measuring fluorescent emissions from the mixture in each of the monomer and excimer emission states; and (f) comparing the intensity of monomer emissions to the intensity of excimer emissions to determine degree of cure.

34. The method set forth in claim 33 further comprising the step of using the determination of the degree of cure for controlling cure of the mixture.

35. A method for determining the degree of cure of a silicone coating comprising:

adding an amount of a reactive fluorescence-tagged silicone polymer reactant able to fluoresce in both monomer and excimer states to a curable silicone coating composition mixture, said reactant containing at least one fluorescent pyrene tag attached to a silicon of the silicone polymer reactant through a (-hydrocarbon—NC=CH—) linkage;

(b) coating the mixture onto a substrate;

(c) curing the mixture;

(d) exposing the mixture to an excitation light source to cause the reactant to fluoresce in the monomer and excimer states;

(e) measuring fluorescent emissions from the mixture in each of the monomer and excimer emission states; and (f) comparing the intensity of monomer emissions to the intensity of excimer emissions to determine degree of cure.

36. The method set forth in claim 33 further comprising the step of using the determination of the degree of cure for controlling cure of the mixture.

37. The method set forth in claim 35 wherein the silicone polymer reactant is a polymer that contains an average of between about one and about five fluorescent pyrene tags per molecule.

38. The method set forth in claim 35 wherein the silicone polymer reactant contains an average of between about one and about three fluorescent pyrene tags per molecule.

39. The method set forth in claim 35 wherein the amount of fluorescent silicone polymer reactant is present in an amount of less than about 50% by weight of the silicone coating mixture.

40. The method set forth in claim 35 wherein the amount of fluorescent silicone polymer reactant is present in an amount of less than about 20% by weight of the silicone coating mixture.

* * * * *

UNITED STATES PATENT AND TRADEMARK OFFICE
CERTIFICATE OF CORRECTION

PATENT NO. : 5,556,663
DATED : September 17, 1996
INVENTOR(S) : Eng-Pi Chang, et. al.

It is certified that error appears in the above-indentified patent and that said Letters Patent is hereby corrected as shown below:

Column 2, line 36, change "siloxanes" to -- siloxane --.
Column 4, line 57, change "fluorphores" to -- fluorophores --.
Column 6, line 20, after "to" and before "one" delete "or".
Column 6, line 21, change "contain" to -- containing --.
Column 6, lines 34-35, change "perfluroalkylethyl" --perfluoroalkylethyl --.
Column 12, line 18, after "together," and before "adhesive" insert
     -- with the - --.

Signed and Sealed this

Third Day of June, 1997

Attest:

BRUCE LEHMAN

Attesting Officer      Commissioner of Patents and Trademarks